US00PP18866P3

(12) United States Plant Patent
Zerr

(10) Patent No.: US PP18,866 P3
(45) Date of Patent: Jun. 3, 2008

(54) POINSETTIA PLANT NAMED 'FISMARS PINK'

(50) Latin Name: *Euphorbia pulcherrima*
Varietal Denomination: Fismars Pink

(75) Inventor: Katharina Zerr, Höhr-Grenzhausen (DE)

(73) Assignee: Florfis AG, Binningen (CH)

( * ) Notice: Subject to any disclaimer, the term of this patent is extended or adjusted under 35 U.S.C. 154(b) by 156 days.

(21) Appl. No.: 11/330,442

(22) Filed: Jan. 12, 2006

(65) Prior Publication Data

US 2007/0163020 P1 Jul. 12, 2007

(51) Int. Cl.
*A01H 5/00* (2006.01)

(52) U.S. Cl. ..... Plt./306
(58) Field of Classification Search ..... Plt./306
See application file for complete search history.

(56) References Cited

U.S. PATENT DOCUMENTS 11,869 A * 10/1854 Fruehwirth ..... 228/153

OTHER PUBLICATIONS

UPOVROM PBR 20040247 Plant Variety Database 2007/01 search for 'Fismars Pink' 1 page.*

Broertjes et al. Application of Mutation Breeding Method in the improvement of Vegetatively Propagated Crops.*

* cited by examiner

*Primary Examiner*—Annette H Para
(74) *Attorney, Agent, or Firm*—Jondle & Associates, P.C.

(57) ABSTRACT

A new Poinsettia plant particularly distinguished by medium size, pink, ovate bracts in a flat, rosette-like arrangement, with deep green foliage, ovate leaves with nearly no lobes, early to medium flowering response and a medium size, V-shape plant habit, is disclosed.

1 Drawing Sheet

Genus and species: *Euphorbia pulcherrima.*
Variety denomination: 'Fismars Pink'.

BACKGROUND OF THE NEW PLANT

The present invention comprises a new and distinct cultivar of poinsettia plant, botanically known as *Euphorbia pulcherrima,* and hereinafter referred to by the cultivar name 'Fismars Pink'. The new cultivar is the result of an induced mutation in the poinsettia plant 'Fismars' (U.S. Plant Pat. No. 14,977) made in the year 2003 in Ahrensburg, Germany.

In May 2003, young plants of 'Fismars' were irradiated with x-rays in Ahrensburg, Germany. The treated plants were grown in Hillscheid, Germany, and were propagated by shoot tip cuttings. The resulting plants were screened for positive mutations and examined during the flowering period in winter 2003/2004. Among these plants a pink-flowered plant was selected and asexually multiplied for further examination in 2004.

The new cultivar was created in 2003 in Ahrensburg, Germany and has been asexually reproduced repeatedly by vegetative cuttings in Hillscheid, Germany over a two-year period. 'Fismars Pink' has not been observed under all possible environmental conditions. The present invention has been found to retain its distinctive characteristics through successive asexual propagations.

Plant Breeder's Rights for this cultivar were applied for in Europe on Feb. 16, 2004 and in Canada on Nov. 17, 2004.

SUMMARY OF THE INVENTION

The following are the most outstanding and distinguishing characteristics of this new cultivar when grown under normal horticultural practices in Hillscheid, Germany.

1. Pink bract color;
2. Medium size, ovate bracts in a flat, rosette-like arrangement;
3. Deep green foliage with ovate leaves that have nearly no lobes;
4. Medium size, V-shaped plant habit; and
5. An early to medium flowering response.

DESCRIPTION OF PHOTOGRAPH

This new poinsettia plant is illustrated by the accompanying photograph which shows overall plant habit including blooms, buds, and foliage of the plant; the colors shown are as true as can be reasonably obtained by conventional photographic procedures. The photograph is of a whole plant about 18-weeks old and in full flower, grown in a greenhouse in Hillscheid, Germany, in early December of 2005.

DESCRIPTION OF THE NEW CULTIVAR

The following detailed descriptions set forth the distinctive characteristics of 'Fismars Pink'. The data which define these characteristics were collected from asexual reproductions carried out in Hillscheid, Germany. The plant history was taken on 18-week old plants which were planted as rooted cuttings in 14-cm pots on Jul. 28, 2005 and were pinched on Aug. 12, 2005, which left 7 to 8 leaves remaining. The plants were grown in a greenhouse at a minimum temperature of 18° C. and a ventilation temperature of 24° C. The plants initiated flowers under natural short-day conditions in fall. No black cloth was applied to the greenhouse to simulate short-day conditions. No growth regulator was applied. Color readings were taken under natural light in the greenhouse. Color references are primarily to the RHS Colour Chart of The Royal Horticultural Society of London (RHS) (2001).

DETAILED BOTANICAL DESCRIPTION OF THE NEW PLANT

Classification:

*Family.*—Euphorbiaceae.

*Botanical.*—*Euphorbia pulcherrima* (Willd. Ex Klotzsch).

*Common name.*—Poinsettia.

Parentage: Mutation of the red-colored poinsettia plant 'Fismars' (U.S. Plant Pat. No. 14,977).

Growth:

*Form.*—Shrub, self-branching.

*Growth and branching habit.*—Medium size and moderately compact; pinched plants are bushy with the branches slanting upright at an angle of about 45°.

*Height* (*from soil line to the top*).—20.3 cm.

*Width.*—43 cm.

*Time to produce a finished flowering plant.*—17 weeks for a 14 cm pot.

*Time to initiate and develop roots.*—20 to 24 days in a greenhouse at 22° C. to 24° C.

Branches:

*Average number.*—7.5.

*Length of branches.*—16 cm to 19 cm.

*Internode length.*—1.5 cm to 3 cm.

*Diameter of branches.*—0.6 cm to 0.7 cm.

*Stem color.*—Upper: Approximately RHS 176D (green, weakly reddish infused). Lower: RHS 143B (green).

Leaves:

*Quantity.*—45 to 55 leaves per plant (6 to 8 leaves per branch).

*Arrangement.*—Alternate.

*Size.*—Length: 11.6 cm. Width: 7.8 cm.

*Shape.*—Ovate.

*Margin.*—Entire.

*Apex.*—Acuminate.

*Base.*—Truncate to obtuse.

*Lobes.*—Few, rounded, relatively shallow.

*Color* (*mature leaves*).—Upper surface: Near RHS 137A and RHS 139A. Lower surface: RHS 137C.

*Color* (*immature leaves*).—Upper surface: RHS 143A. Lower surface: RHS 137D.

*Texture.*—Upper surface: Smooth and flat, no rugosity, only weakly veined. Lower surface: Flat and smooth, except for the slightly protruding midrib and finer side veins in a pinnate pattern.

*Venation color.*—Upper surface: RHS 143C (green). Lower surface: RHS 145B (pale green).

*Variegation.*—None.

*Leaf petiole.*—Length: 5.5 cm. Diameter: 0.3 cm. Color: Upper surface: RHS 146B (dull green). Lower surface: RHS 145A (light green). Texture: Glabrous. Aspect: Horizontally directed, leaf blades slanting somewhat downward.

Bracts:

*Number per inflorescence.*—12 to 14.

*Shape.*—Ovate.

*Base.*—Larger: Obtuse. Younger: Acute.

*Apex.*—Acuminate.

*Lobes.*—Rounded, very weak to weak.

*Size.*—Length: 12.0 cm. Diameter: 8.1 cm.

*Texture.*—Mostly smooth, little rugosity with younger bracts (not fully expanded).

*Bract color.*—Upper surface: RHS 55A (pink) for larger and lower bracts; closer to RHS 51A for younger bracts; closer to RHS 53D for smallest bracts.

*Vein color.*—Upper surface: Corresponds closely to the bract color. Lower surface: RHS 47D (reddish) near base.

*Bract petiole.*—Length: 1.0 cm to 1.5 cm. Color: Upper surface: RHS 47A (red). Lower surface: RHS 47D.

Inflorescence:

*Blooming habit.*—Beginning under natural short-day conditions in the Fall: Botanically (cyathia open): Late November. Commercially (bracts colored, marketable): November 20.

*Inflorescence type.*—Medium size, flat with the bracts mostly horizontally directed, in the center a tight cyme with medium size cyathia.

*Average number of inflorescences.*—7.2.

*Lastingness.*—About 4 weeks with no dropping of bracts.

*Diameter.*—20 cm to 23 cm.

*Height.*—3.0 cm to 3.5 cm.

Cyme:

*Cyme diameter.*—About 2.5 cm.

*Cyathia number.*—5 to 7 in a tight cluster.

*Cyathium.*—Shape: Ovate. Diameter: 0.5 cm. Length: 0.6 cm to 0.7 cm. Color: Mainly RHS 143B (green); top is RHS 46D (red).

*Peduncle.*—Color: RHS 143C (light green). Length: 0.2 cm to 0.3 cm.

*Nectar cups.*—Number: Usually only one per cyathium. Size: Up to 0.6 cm wide. Color: RHS 15A (golden-yellow).

Reproductive organs:

*Stamens.*—Number: 10 to 15 in a cluster. Filaments: Color: RHS 46B (red). Length: 0.2 cm to 0.3 cm. Pollen color: RHS 12A (yellow).

Fruit and seed set: No seed set observed so far.

Disease and insect resistance: No particular resistance or susceptibility has been observed.

COMPARISON WITH PARENTAL AND COMMERCIAL CULTIVARS

'Fismars Pink' differs from the parental cultivar 'Fismars' (U.S. Plant Pat. No. 14,997) by having pink instead of red bract color and a more compact plant habit than 'Fismars'.

'Fismars Pink' differs from the commercial cultivar 'Fiscorosa' (U.S. Plant Pat. No. 10,077), by having shorter bracts, inflorescences with fewer cyathia and a more compact plant habit than 'Fiscorosa'.

'Fismars Pink' differs from the commercial cultivar 'Eckalbert' (U.S. Plant Patent applied for) by having flatter inflorescences with shorter and more horizontally directed bracts while 'Eckalbert' has more funnel-shaped inflorescences. In addition, the leaves and bracts of 'Fismars Pink' develop nearly no lobes, while 'Eckalbert' shows a moderate oak leaf shape. 'Fismars Pink' also has a later flowering response of 4 to 8 days compared to 'Eckalbert'.

I claim:

1. A new and distinct cultivar of Poinsettia plant as shown and described herein.

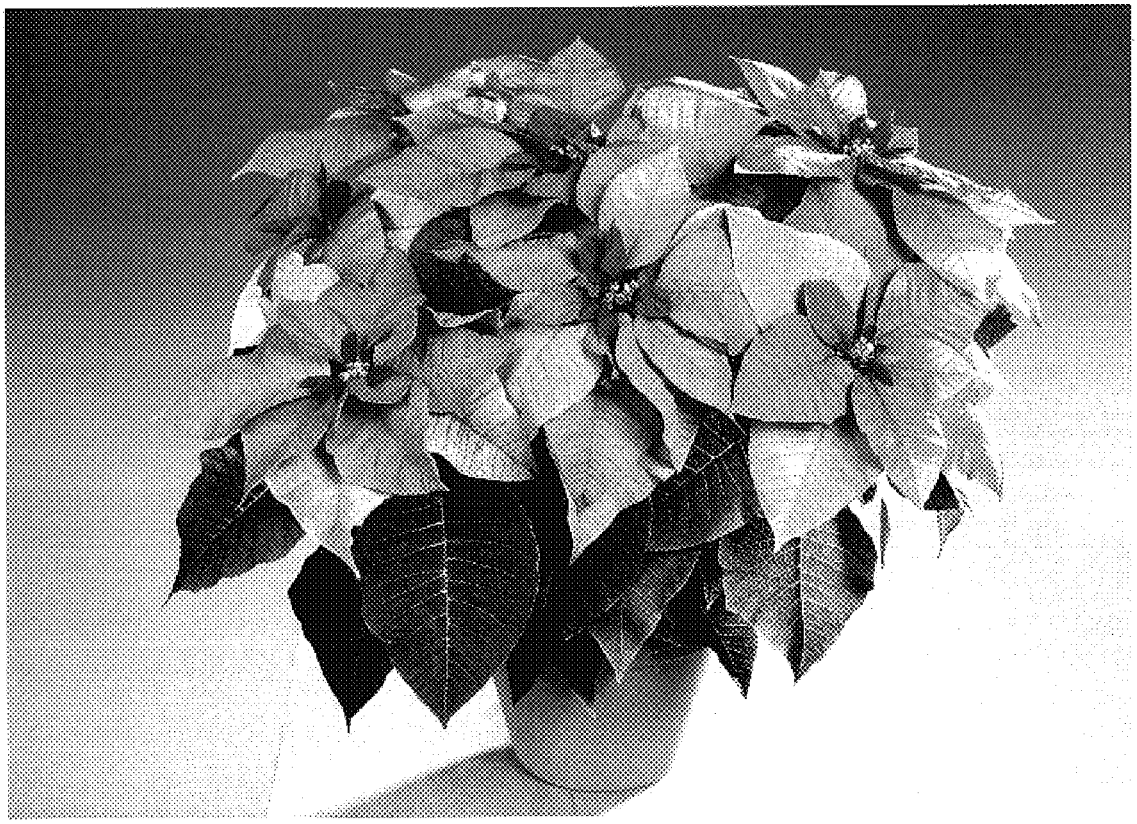

* * * * *